United States Patent
Gao et al.

(10) Patent No.: US 11,685,931 B2
(45) Date of Patent: Jun. 27, 2023

(54) **APPLICATION OF A FRAGMENT OF AN ISOLATED NUCLEOTIDE SEQUENCE IN CONSTRUCTION OF NON-MINERALIZED INTERMUSCULAR BONE OF *DANIO RERIO***

(71) Applicants: Hubei Hongshan Laboratory, Hubei (CN); Huazhong Agricultural University, Hubei (CN)

(72) Inventors: Zexia Gao, Hubei (CN); Chunhong Nie, Hubei (CN); Shiming Wan, Hubei (CN); Yulong Chen, Hubei (CN); Dejie Zhu, Hubei (CN)

(73) Assignees: Hubei Hongshan Laboratory, Hubei (CN); Huazhong Agricultural University, Hubei (CN)

( * ) Notice: Subject to any disclaimer, the term of this patent is extended or adjusted under 35 U.S.C. 154(b) by 0 days.

(21) Appl. No.: 17/554,881

(22) Filed: Dec. 17, 2021

(65) Prior Publication Data

US 2022/0275394 A1    Sep. 1, 2022

(30) Foreign Application Priority Data

Oct. 19, 2020 (CN) .......................... 202011115842.3

(51) Int. Cl.
| | |
|---|---|
| *C12N 15/85* | (2006.01) |
| *A01K 67/027* | (2006.01) |
| *C12N 9/22* | (2006.01) |
| *C12N 15/11* | (2006.01) |

(52) U.S. Cl.
CPC ...... *C12N 15/8509* (2013.01); *A01K 67/0275* (2013.01); *C12N 9/22* (2013.01); *C12N 15/11* (2013.01); *A01K 2217/077* (2013.01); *A01K 2227/40* (2013.01); *C12N 2310/20* (2017.05); *C12N 2800/80* (2013.01)

(58) Field of Classification Search
None
See application file for complete search history.

(56) References Cited

PUBLICATIONS

S.S. Brooks et al., "A Novel Ribosomopathy Caused by Dysfunction of RPL10 Disrupts Neurodevelopment and Causes X-Linked Microcephaly in Humans," Genetics, vol. 198, 723-733 (Oct. 2014).
Nie, Chunhong et al., "Ossification patterns of intermuscular bones in different fish species," Acta Hydrobiologica Sinica, vol. 42, No. 1, pp. 131-137 (Jan. 2018).
Perazza et al., "Lack of intermuscular bones in specimens of Colossoma macropomum: An unusual phenotype to be incorporated into genetic improvement programs," Aquaculture, vol. 47, Supplement 1, pp. 57-60 (Apr. 1, 2017).
Xu, X.F., et al., "Normally grown and developed intermuscular bone-deficient mutant in grass carp, Ctenopharyngodon idellus," Chinese Scientific Bulletin, vol. 60, pp. 52-57, doi: 10.1360/N972014-00637 (2015).
Wan, S., et al., "Identification of MicroRNA for Intermuscular Bone Development in Blunt Snout Bream (*Megalobrama amblycephala*)," International Journal of Molecular Sciences, vol. 16, pp. 10686-10703 (May 2015).
Nie, Chunhong, et al., "Comparative proteomics analysis of teleost intermuscular bones and ribs provides insight into their development," BMC Genomics, vol. 18, pp. 147-160 (14 pages) (2017).
Wan, S., et al., "Dynamic mRNA and miRNA expression analysis in response to intermuscular bone development of blunt snout bream (*Megalobrama amblycephala*)," Scientific Reports, vol. 6, pp. 31050—(13 pages) (Aug. 2016).
Wan, S., et al., "Identification and mapping of SNPs associated with number of intermuscular bone in blunt snout bream," Aquaculture, vol. 507, pp. 75-82 (May 30, 2019).
Liang, P., et al., "CRISPR/Cas9-mediated gene editing in human tripronuclear zygotes," Protein Cell, vol. 6, No. 5, pp. 363-372 (2015).
Zhang, L. et al., "Large Genomic Fragment Deletions and Insertions in Mouse Using CRISPR/Cas9," PLoS ONE 10(3): e0120396. doi:10.1371/journal.pone.0120396 (2015).
Port, F., et al., "Augmenting CRISPR applications in *Drosophila* with tRNAflanked Cas9 and Cpf1 sgRNAs," Nat. Methods, vol. 13, No. 10, pp. 852-854 (Oct. 2016).
Xie, S., et al., "A novel technique based on in vitro oocyte injection to improve CRISPR/Cas9 gene editing in zebrafish," Scientific Reports, vol. 6, pp. 34555—(10 pages0 (Sep. 2016).

*Primary Examiner* — Allison M Fox
*Assistant Examiner* — Alyssa G Weston
(74) *Attorney, Agent, or Firm* — Mei & Mark LLP; Manni Li

(57) ABSTRACT

Application of a fragment of an isolated nucleotide sequence in the construction of zebrafish without intermuscular bones. The nucleotide sequence is shown in SEQ ID NO:1. Gene mutation is performed by taking SEQ ID NO:1 as a target gene; the mutant F0 embryos are selected and cultured to adult fish; F0 mutant is hybridized with wild type zebrafish to generate an F1 embryos; sense mutant heterozygotes F1 is screened out and cultured to adult fish; and then F1 heterozygote self-crosses to generate F2 generation of three gene types, including homozygote, heterozygote, and wild type. Zebrafish without intermuscular bones is obtained by using a gene mutation method, which provided a basis for subsequent research on a molecular formation mechanism of fish intermuscular bones and the cultivation of economic fishes without intermuscular bone and possessed a basic research value and an application value in other economic aquaculture fish species.

4 Claims, 2 Drawing Sheets
Specification includes a Sequence Listing.

WT: SEQ ID NO.1
TCAGCGGAGCTCAGGAATGCCTCAGGGGTTATGAAGAACCAGGTGGC
Mutant: SEQ ID NO.2
TCAG------------------------------------------GGGTTATGAAGAACCAGGTGGC
FIG. 1
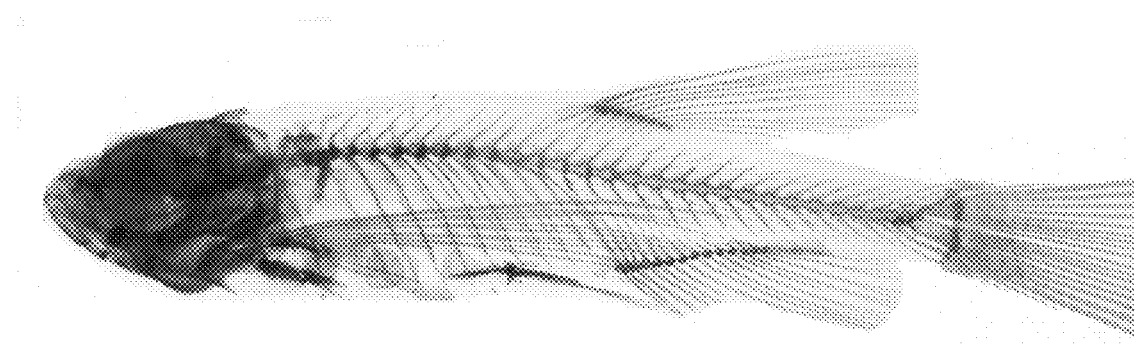
FIG. 2
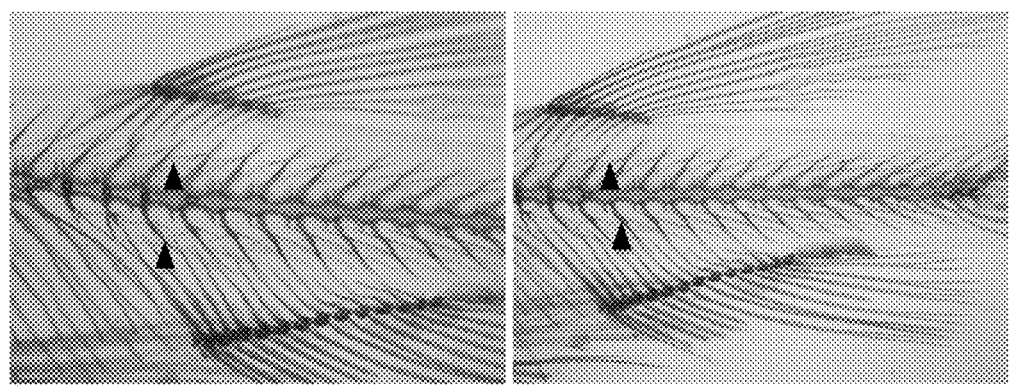
FIG. 3A          FIG. 3B

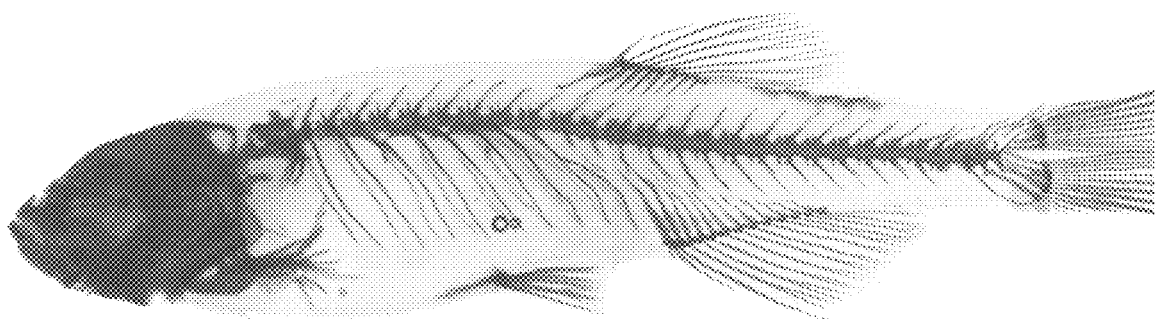
FIG. 4
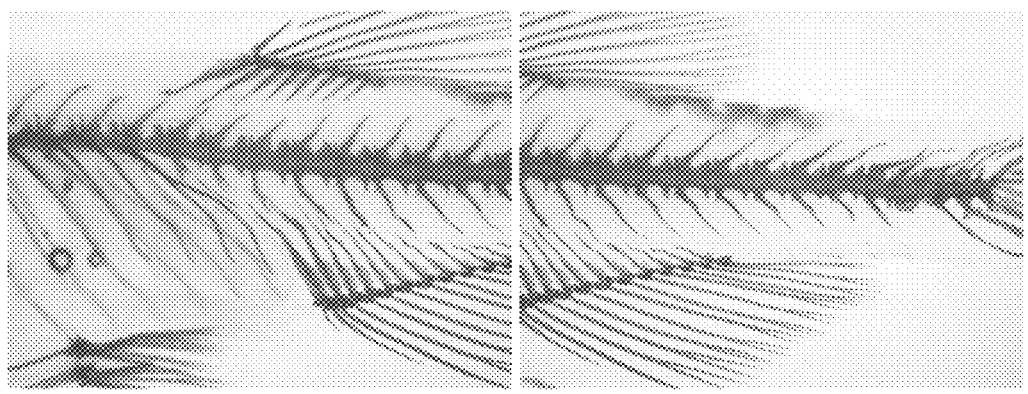
FIG. 5A
FIG. 5B

APPLICATION OF A FRAGMENT OF AN ISOLATED NUCLEOTIDE SEQUENCE IN CONSTRUCTION OF NON-MINERALIZED INTERMUSCULAR BONE OF *DANIO RERIO*

CROSS-REFERENCE TO RELATED APPLICATIONS

The subject application claims priority on Chinese patent application no. 202011115842.3 filed on Oct. 19, 2020 in China. The contents and subject matters of the Chinese priority application is incorporated herein by reference.

BACKGROUND OF THE INVENTION

Technical Field

The present invention belongs to the field of molecular biology, and specifically relates to the application of an isolated nucleotide sequence fragment in the construction of intermuscular boneless of zebrafish. By mutating the nucleotide sequence, non-mineralized intermuscular bones of zebrafish may be obtained.

Description of Related Art

Fish intermuscular bones, which only occur in the myosepta of basal teleosts, are small spicule-like bones generated from tendon differentiation, and are divided into three types based on different attachment position in fish body: epineurals, epicentrals, and epipleurals. The presence of the intermuscular bones has a great relationship with a taxonomic status of fishes. In fish evolution, the numbers of intermuscular bones have undergone changes from a few to many, then to a few, and finally, to none. Most aquaculture fish species in China have a certain number of intermuscular bones, such as common carp (*Cyprinus carpio*), grass carp (*Ctenopharyngodon idellus*), crucian carp (*Carassius carassius*), tambaqui (*Colossoma macropomum*), etc. The presence of intermuscular bones in cultured finfish species and their negative effect had been paid much attention since 1939. These small IBs negatively affect the economic value of fish species, restrict processing options, stress consumers due to the possibility of injury or trauma if lodged in the throat or mouth, and consequently affect the market value of the fish, especially cyprinid species. The discovery of the tambaqui individuals without intermuscular bones in one Brazil aquaculture farm proved that the intermuscular bone has no significant effect on the life activities of the fish itself (Perazza et al., 2017). In China, studies showed that the growth and development of grass carp without intermuscular bone obtained by gynogenesis screening was normal (Xu et al., 2015). Therefore, to a certain extent, it is feasible to remove or reduce the number of intermuscular bones in fishes. Existed studies have shown that molecular genetic information related to the development and the number of intermuscular bones has been excavated (Wan et al., 2015; Wan et al., 2016; Nie et al., 2017; Wan et al., 2019), and provide a genetic data basis for intermuscular bone research. However, key genes directly related to the development of intermuscular bones are not screened out.

Zebrafish (*Danio rerio*), a tropical ornamental fish, belongs to Cyprinidae. The zebrafish is a classical-model animal for research on vertebrate embryology and developmental genetics (Brooks et al., 2014). The genome and transcriptome data of the zebrafish are relatively complete, and it has many advantages for gene-editing studies, such as high fecundity, high survival rate, fertilization in vitro, eggs' diameters being about 1 mm and easy for microinjection. The study shows that the types and ossification model of intermuscular bones in zebrafish are similar to those of Cyprinidae species (Nie et al., 2018). Therefore, the key genes screened out for the non-mineralized intermuscular bone in zebrafish has the great potential to be used in other economic aquaculture fish species.

Clustered Regularly Interspaced Short Palindromic Repeats (CRISPR)/CRISPR-associated (Cas9) is a new-generation gene editing technology, which has the characteristics of simple production, convenient use, low cost, and high efficiency (Mussolino & Cathomen, 2013). To date, the CRISPR/Cas9 technology has been proven to be effective in many species, including mammals, microorganisms, plants, and fishes (Liang et al., 2015; Zhang et al., 2015; Port&Bullock, 2016; Xie et al., 2016). The CRISPR/Cas9 gene editing technology provides an efficient way to screen out the key regulatory genes for the development of intermuscular bones in fish and to breed the new intermuscular boneless strains of fishes.

BRIEF SUMMARY OF THE INVENTION

The present invention aims to provide the application of one separated nucleotide sequence in the construction of intermuscular boneless of zebrafish. The nucleotide sequence of gene is as shown in SEQ ID NO:1. Using SEQ ID NO:1 as the target sequence, zebrafish without intermuscular bones can be obtained by gene mutation, and the method is feasible and simple in operation.

Another objective of the present invention is to provide a mutant gene sequence included in the zebrafish line without intermuscular bones. The gene sequence is shown in SEQ ID NO:2.

To achieve the objective, the present invention adopts the following technical measures:

The present invention provides an application of one segment of a separated nucleotide sequence in the construction of zebrafish without intermuscular bones. The nucleotide sequence is shown in SEQ ID NO:1.

In the application, preferably, the target nucleotide sequence of gene is shown in SEQ ID NO:3.

In the application, mutation is performed on the sequence as shown in SEQ ID NO:1, and the mutated sequence is as shown in SEQ ID NO:2.

In the application, after the sequence shown in SEQ ID NO:1 is mutated, F0 mutants with mutations are screened out; the mutant is hybridized with wild-type zebrafish to generate an F1 generation, which is cultivated to an adult fish. Heterozygotes with mutants in F1 generation are screened out, and the heterozygote self-crosses to produce F2 generation, and homozygotes in the F2 generation are the zebrafish without intermuscular bones.

In the application, preferably, gene editing is performed by taking the sequence as shown in SEQ ID NO:1 as a target site through a CRISPR/Cas9 method.

In the application, preferably, the intermuscular boneless line includes a gene sequence as shown in SEQ ID NO:2.

In the application, preferably, CRISPR/Cas9 editing includes the following steps: sgRNA is amplificated by overlap PCR with a conservative downstream primer Scaffold of SEQ ID NO: 4 having the sequence of (GATCCGCACCGACTCGGTGCCACTTTTTCAAGTT-GATAACG GACTAGCCTTATTTTAACTTGCTAT-TTCTAGCTCTAAAAC) and an upstream primer with a T7 promoter that specifically contains a target sequence of SEQ ID NO:5 having the sequence of (AATTAATACGACTCACTATAGGGGAACATCGGTGAGTCTGGTTTTAGAGC TAGAAATAGC), and transcribed with transcription kit in vitro. Cas9mRNA is transcribed with linearized pT3TS-nCas9n plasmid in vitro; sgRNA and zCas9mRNA are injected into the zebrafish embryo in a one-cell stage; F0 mutants with mutations are screened out; the mutant is hybridized with wild-type zebrafish to generate an F1 generation, which is cultivated to adult fish. Heterozygotes with mutants in F1 generation are screened out, and the heterozygote self-crosses to produce F2 generation, and homozygotes in the F2 generation are the zebrafish without intermuscular bones.

The protective content of the present invention also includes screening out a segment homologous with SEQ ID NO:1 in fishes with intermuscular bone, and mutating the homologous segment to obtain a corresponding fish without intermuscular bone.

Compared with the prior technology, the present invention has the following advantages:

The method in the present application can be used for obtaining the zebrafish line without intermuscular bones. The method is easy and feasible, and simple to operate. The zebrafish line without intermuscular bones obtained by using a gene mutation method possess basic value and an application value of scientific research on the fish intermuscular bone development. The method can be used for obtaining the zebrafish line without intermuscular bones.

BRIEF DESCRIPTION OF THE SEVERAL VIEWS OF THE DRAWINGS

FIG. 1 shows the target gene sequence of zebrafish and the mutated sequence in the present invention.

FIG. 2 shows the whole-skeletal staining of a wild type zebrafish using alizarin red staining method.

FIGS. 3A and 3B show the intermuscular bones stained by alizarin red in the dorsal (FIG. 3B) and tail (FIG. 3A) parts of wild type zebrafish, where the arrows indicate the mineralized intermuscular bones.

FIG. 4 shows the whole-skeletal staining picture of homozygous mutant zebrafish using alizarin red staining method.

FIGS. 5A and 5B show that no intermuscular bones are stained by alizarin red in the dorsal (FIG. 5B) and tail (FIG. 5A) parts of homozygous mutant zebrafish in the present invention.

DETAILED DESCRIPTION OF THE INVENTION

Unless otherwise specified, the technical solutions of the present invention are conventional methods in the field; the reagents or materials used, unless otherwise specified, are all derived from commercial channels. In the embodiment of the present invention, zebrafish without intermuscular bones is prepared by performing mutation on a target sequence with a CRISPR/Cas9 method, and other gene editing methods in the field are only mutations for SEQ ID NO:1. The mutation in the present invention includes missense mutation, frameshift mutation, etc. As long as the edited amino acid sequence after the mutation is different from the amino acid sequence edited by SEQ ID NO: 1, the zebrafish line without intermuscular bones can be successfully prepared.

Example 1. Application of One Separated Nucleotide Sequence in the Construction of Zebrafish Line without Intermuscular Bones 1.1 Experimental materials: Wild fluorescent zebrafish Tg (sp7:eGFP) are raised in a fish house of College of Fisheries of Huazhong Agricultural University under the conditions at 28° C. room temperature and 14:10 photoperiod. The embryos used for microinjection are obtained by the natural spawning of female and male zebrafish.

1.2 Experimental method 1.2.1 Determination of sgRNA target site: The sgRNA target site is determined as 5'AGCTCAGGAATGCCTCAG'3 of SEQ ID NO: 3.

1.2.2 sgRNA synthesis in vitro: The sgRNA is amplificated by overlap PCR with a conservative downstream primer Scaffold of SEQ ID NO: 4 having a sequence of (GATCC GCACCGACTCGGTGCCACTTTTTCAAGTT-GATAACGGACTAGCCTTATTTTAACTTGC TAT-TTCTAGCTCTAAAAC) and an upstream primer with a T7 promoter that specifically contains a target sequence of SEQ ID NO: 5 having a sequence of (AATTAATACGACTCACTATAGGGGAACATCGGTGAGTCTGGTTTTAGAGC TAGAAATAGC).

The PCR system is set as follows: 10.5 μL of Primer STAR Max DNA Polymerase, 5 μL of Scaffold, 5 μL of sgRNA, and 4.5 μL of ddH$_2$O. The PCR reaction conditions are as follows: pre-denaturing for 30s at 98° C., denaturing for 10s at 98° C., annealing for 10s at 60° C., extending for 15s at 72° C., 45 cycles, and extending again for 5 min at 72° C. 1 μL of PCR product is taken to test with 2% agarose gel electrophoresis. The PCR product is purified after the strip size being verified to be correct, and the concentration is measured with Nanodrop 2000 (Thermo Scientific, USA). DNA template of sgRNA is transcribed with a Transcrip-tAID T7 High Yield Transcription Kit (Thermo scientific, USA), and is purified with RNA purification kit (ZYMO, USA). 1 μL sgRNA is taken to measure RNA concentration with Nanodrop 2000 (Thermo Scientific, USA) and RNA quality with 2% agarose gel electrophoresis, respectively, and finally stored at −80° C.

1.2.3 zCas9mRNA transcription in vitro: XbaI restriction endonuclease (NEB, USA) is used to linearize pT3TS-nCas9n plasmid, and linearized pT3TS-nCas9n plasmid is purified with Gel Extraction Kit (Omega, USA) after complete linearization being checked through 1% agarose gel electrophoresis. The zCas9mRNA is transcribed in vitro according to the instructions of the mMESSAGE mMA-CHINE T3 Transcription Kit (Invitrogen, USA), and is purified through a lithium chloride precipitation method. zCas9mRNA is dissolved in Nuclease-free water and measured concentration by Nanodrop 2000 (Thermo Scientific, USA), and detected zCas9mRNA quality through 2% agarose gel electrophoresis. Finally, the zCas9mRNA is subpackaged and stored at −80° C. for later use.

1.2.4 Microinjection: In the evening before injection, male and female zebrafish are matched in a proportion of 3:2 and are separated through a spacer plate. The spacer plate is pulled out 30 min before injection next day to allow them to spawn naturally. Embryos are collected 20 min later and sequentially arranged in an embryo mold. 5 μL of an injection sample is prepared with sgRNA and zCas9mRNA, where a final concentration of sgRNA is 80 ng/μL and a final concentration of zCas9mRNA was 500 ng/μL; and phenol red with a final concentration of 0.2% is added as an indicator. An experimental sample is injected into the zebrafish embryo at one-cell stage through a Picoliter Microinjector (PLI-100A, Warner, USA). The injected zebrafish embryo is cultured with 0.01% methylene blue culture solution, and is put in a constant temperature incubator with light at 28° C.

1.2.5 Detection of the target site mutation rate: About 30 embryos after 48 h injection are selected, and the genome DNA of the zebrafish embryos are quickly extracted with Lysis buffer. The embryos to be lysed are put into a 200 μL 96-well plate with 50 μL of Lysis buffer (10 mmol/L Tris+50 mmol/LKCl+1.5 mmol/L $MgCl_2$+0.3% Tween-20+0.3% Nonident P-40). PCR reaction is performed for 20 min at 94° C., and is ended at 55° C.; and then 5 μL of PK enzyme (10 mg/ml) is added on ice and vortex to mix well, followed PRC reaction is performed for 60 min at 55° C., performed for 20 min at 94° C., and ended at 16° C. A 187 bp product size near the target site is amplified with a target site amplification detection primer (check F: 5'TGTATCTTGTTCTCTCCACAGG of SEQ ID NO:6; and check R: 5'TGTACTGACCTCTTCCGCTTC of SEQ ID NO:7). The PCR reaction system is as follows: 10 μL of 2×Hieff® PCR Master Mix (Yisheng, Shanghai), 0.5 μL of the upstream primer, 0.5 μL of the downstream primer, 2 μL of a genome DNA template and 7 μL of sterile water. The PCR reaction conditions are as follows: pre-denaturing for 5 min at 94° C., denaturing for 30 s at 94° C., annealing for 30 s at 54° C., extending for 30 s at 72° C., circulating for 35 times, and extending again for 5 min at 72° C. 10 μL of the PCR product is taken to test with 3% agarose gel electrophoresis, hybrid individuals F0 with double stripes near the PCR product are picked out and cultured to adult fish. The mutation rate of 30 embryos is about 30%.

1.2.6 Acquisition of heterozygotes F1: F1 generation individuals are obtained by crossing F0 and wild type; embryo DNA of F1 generation is extracted; PCR product amplification is preformed through a target site detection primer, and mutant heterozygotes F1 are screened out with 3% agarose gel electrophoresis. A 417 bp product size near the target site is amplified with a target site amplification sequencing primer (seq F: 5'GACCAAACCCCTCTAAA of SEQ ID NO:8; seq R: 5'CGAGTACTTGATGAACGCT of SEQ ID NO:9). 2 μL of the PCR product is taken to detect with 1% agarose gel electrophoresis, and the single-stripe product with a correct size is detected and sent to the company for sequencing (Qingke Biotechnology Co., Ltd., Wuhan). Sequences of each mutant individual are compared and analyzed with wild type zebrafish gene sequences.

1.2.7 Acquisition of homozygous F2: The acquired F1 individuals of the same mutant type are cultured to adult fish, and the heterozygous F1 self-cross to produced F2 generation with three gene types: homozygous, heterozygous and wild-type. Zebrafish without intermuscular bones is obtained by determining gene mutant sequence of F2 generation homozygous through genotyping.

1.2.8 Phenotype and genotype analysis of the zebrafish without intermuscular bones: Compared results of the target site sequences of the gene in wild type zebrafish and the zebrafish without intermuscular bones are shown in FIG. 1. SEQ ID NO:1 shows a target site sequence of wild type zebrafish, and SEQ ID NO:2 shows a target site sequence of zebrafish without intermuscular bones.

The phenotype of the intermuscular bones of the zebrafish is observed through a whole-mount skeletal staining method using alizarin red (the adult fish is rinsed for 30 min in $ddH_2O$ water after being fixed for 48 h in 4% paraformaldehyde, following rinsed for 4 h in an equal-volume mixed solution of 3% $H_2O_2$ and 1% KOH, rinsed for 30 min in $ddH_2O$, treated for 12 h in a saturated borax solution, rinsed for 30 min in $ddH_2O$, stained for 24 h in a mixed solution of 1% alizarin red S (Sigma) and 1% KOH, rinsed for 1 h in $ddH_2O$ until the alizarin red dye liquor is cleaned, and rinsed for 24-48 h in a mixed solution of 1% trypsin (Solarbio) and 2% saturated borax solution; the gradient is transparent in 50% and 100% glycerol, stored in 100% glycerol).

The phenotype of whole intermuscular bones of the wild type zebrafish is shown in FIG. 2, the remarkable number of intermuscular bones are distributed on the dorsal and tail of the wild type zebrafish. The total number of intermuscular bones in each individual is about 76-80 (FIGS. 2, 3A, and 3B). The phenotype of whole intermuscular bones in homozygote mutant zebrafish is shown in FIG. 4. The mineralized intermuscular bones have disappeared (FIGS. 4, 5A, and 5B). Sequencing analysis shows that the stably-inherited intermuscular boneless is derived from mutants of one type. Compared with sequence as shown in SEQ ID NO: 1, the sequence near the target sequence is mutated to the sequence as shown in SEQ ID NO: 2, resulting in frameshift mutation.

What is claimed is:

1. A method for constructing a zebrafish without intermuscular bones, comprising:
    performing a mutation on a target sequence of SEQ ID NO:1 in the zebrafish, thereby obtaining a mutated sequence of SEQ ID NO: 2 in the zebrafish.

2. The method according to claim 1, wherein the mutation is performed by adopting a CRISPR/Cas9 editing method.

3. The method according to claim 2, further comprising:
    screening out an F0 mutant with the SEQ ID NO: 2 mutation;
    hybridizing the F0 mutant with a wild zebrafish to generate an F1 generation;
    cultivating the F1 generation to adult fish and screening out F1 generation heterozygotes with the SEQ ID NO: 2 mutation;
    performing F1 heterozygote self-cross to generate an F2 generation; and obtaining homozygotes in the F2 generation that are zebrafish without intermuscular bones.

4. The method according to claim 3, wherein the CRISPR/Cas9 editing method further comprises the following steps:
    amplifying an sgRNA by overlap PCR with a conservative downstream primer scaffold having a sequence of SEQ ID NO: 4 and an upstream primer with a T7 promoter that specifically contains a target sequence of SEQ ID NO: 5, and transcribing with a transcription kit in vitro;
    transcribing a zCas9mRNA with a linearized pT3TS-nCas9n plasmid in vitro;
    injecting the sgRNA and zCas9mRNA into a zebrafish embryo in a one-cell stage;
    screening out F0 mutants with the SEQ ID NO: 2 mutation;
    hybridizing the F0 mutants with wild-type zebrafish to generate an F1 generation;
    cultivating the F1 generation to adult fish and screening out heterozygotes with the same mutant gene type as in the F1 generation;
    performing self-cross on the heterozygotes to produce an F2 generation; and
    obtaining homozygotes after genetic typing in the F2 generation, wherein homozygotes are zebrafish without intermuscular bones.

* * * * *

SEQUENCE LISTING

<160> NUMBER OF SEQ ID NOS: 9

<210> SEQ ID NO 1
<211> LENGTH: 47
<212> TYPE: DNA
<213> ORGANISM: Artificial Sequence
<220> FEATURE:
<223> OTHER INFORMATION: target sequence

<400> SEQUENCE: 1
tcagcggagc tcaggaatgc ctcaggggtt atgaagaacc aggtggc        47

<210> SEQ ID NO 2
<211> LENGTH: 26

```
<212> TYPE: DNA
<213> ORGANISM: Artificial Sequence
<220> FEATURE:
<223> OTHER INFORMATION: mutant sequence

<400> SEQUENCE: 2
tcaggggtta tgaagaacca ggtggc                                    26

<210> SEQ ID NO 3
<211> LENGTH: 18
<212> TYPE: DNA
<213> ORGANISM: Artificial Sequence
<220> FEATURE:
<223> OTHER INFORMATION: target sequence

<400> SEQUENCE: 3
agctcaggaa tgcctcag                                             18

<210> SEQ ID NO 4
<211> LENGTH: 81
<212> TYPE: DNA
<213> ORGANISM: Artificial Sequence
<220> FEATURE:
<223> OTHER INFORMATION: downstream primer

<400> SEQUENCE: 4
gatccgcacc gactcggtgc cacttttca agttgataac ggactagcct tattttaact 60
tgctatttct agctctaaaa c                                         81

<210> SEQ ID NO 5
<211> LENGTH: 60
<212> TYPE: DNA
<213> ORGANISM: Artificial Sequence
<220> FEATURE:
<223> OTHER INFORMATION: upstream primer

<400> SEQUENCE: 5
aattaatacg actcactata ggagctcagg aatgcctcag gttttagagc tagaaatagc 60

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
tgtatcttgt tctctccaca gg                                        22

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
tgtactgacc tcttccgctt c                                         21

<210> SEQ ID NO 8
<211> LENGTH: 18
<212> TYPE: DNA
<213> ORGANISM: Artificial Sequence
<220> FEATURE:
<223> OTHER INFORMATION: primer
```

```
<400> SEQUENCE: 8
gaccaaaccc cctctaaa                                                    18

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
cgagtacttg atgaacgct                                                   19
```